United States Patent [19]
Audousset et al.

[11] Patent Number: 5,804,171
[45] Date of Patent: Sep. 8, 1998

[54] COMPOSITION FOR THE OXIDATION DYEING OF KERATINOUS FIBRES AND DYEING PROCESS EMPLOYING THIS COMPOSITION

[75] Inventors: Marie-Pascale Audousset, Asnieres; Jean Cotteret, Verneuil Sur Seine, both of France

[73] Assignee: L'Oreal, Paris, France

[21] Appl. No.: 589,372

[22] Filed: Jan. 22, 1996

[30] Foreign Application Priority Data

Jan. 20, 1995 [FR] France .................. 95-00663

[51] Int. Cl.⁶ .................. A61K 7/13; A61K 7/06
[52] U.S. Cl. .................. 424/70.1; 8/408
[58] Field of Search .................. 424/70.1; 8/408

[56] References Cited

U.S. PATENT DOCUMENTS

| | | | |
|---|---|---|---|
| 5,261,926 | 11/1993 | Lang | 8/406 |
| 5,344,464 | 9/1994 | Madrane | 8/410 |
| 5,391,206 | 2/1995 | Cotteret | 8/408 |
| 5,443,596 | 8/1995 | Junino | 8/442 |
| 5,451,236 | 9/1995 | Junino | 8/408 |
| 5,478,359 | 12/1995 | La Grange | 8/412 |
| 5,494,490 | 2/1996 | Audousset | 8/409 |
| 5,505,741 | 4/1996 | Junino | 8/408 |
| 5,514,188 | 5/1996 | Cotteret | 8/412 |
| 5,534,036 | 7/1996 | Junino | 8/411 |
| 5,542,952 | 8/1996 | Genet | 8/410 |
| 5,567,421 | 10/1996 | Cotteret | 424/70.1 |
| 5,578,087 | 11/1996 | Audoussett | 8/409 |

FOREIGN PATENT DOCUMENTS

| | | |
|---|---|---|
| A-0428441 | 5/1991 | European Pat. Off. . |
| A-0465340 | 1/1992 | European Pat. Off. . |
| A-3031709 | 4/1982 | Germany . |
| A-3743769 | 7/1989 | Germany . |
| A-3942294 | 6/1991 | Germany . |

*Primary Examiner*—Sally Gardner-Lane
*Attorney, Agent, or Firm*—Finnegan, Henderson, Farabow, Garrett & Dunner, L.L.P.

[57] ABSTRACT

The present invention relates to a composition for the oxidation dyeing of keratinous fibres, especially human keratinous fibres such as hair, comprising an oxidation dye precursor chosen from 3-fluoro-4-aminophenol, N,N'-bis(β-hydroxyethyl)-N,N'-bis(4'-aminophenyl)-1,3-diamino-2-propanol and their addition salts with an acid, in combination with 4-hydroxyindole, as well as to the dyeing process employing this composition with an oxidizing agent.

18 Claims, No Drawings

COMPOSITION FOR THE OXIDATION DYEING OF KERATINOUS FIBRES AND DYEING PROCESS EMPLOYING THIS COMPOSITION

The present invention relates to a composition for the oxidation dyeing of keratinous fibres, especially human keratinous fibres such as hair, comprising a suitably selected oxidation dye precursor in combination with 4-hydroxyindole, as well as to the dyeing process employing this composition with an oxidizing agent.

It is known to dye keratinous fibres and especially human hair, with dyeing compositions containing oxidation dye precursors, especially ortho- or para-phenylenediamines and ortho- or para-aminophenols, generally referred to as oxidation bases. Oxidation dye precursors, or oxidation bases, are colourless or faintly coloured compounds which, when combined with oxidizing products, can give rise by an oxidative condensation process to coloured and colouring compounds.

It is also known that the shades obtained with these oxidation bases can be varied by combining them with dyeing couplers or modifiers, the latter being chosen, in particular, from meta-aminophenols, meta-diphenols, aromatic meta-diamines and certain indole compounds such as 4-hydroxyindole.

The variety of molecules employed as oxidation bases and as couplers enables a rich palette of colours to be obtained.

The so-called "permanent" dyeing obtained by means of these oxidation dyes has, moreover, to satisfy a number of requirements. Thus, it must have no drawback from a toxicological standpoint, and must enable shades to be obtained in the desired intensity and display good staying power when exposed to external agents (light, inclement weather, washing, permanent-waving, perspiration, friction).

The dyes must also enable white hair to be covered, and must lastly be as little selective as possible, that is to say enable the smallest possible deviations of coloration to be obtained over the entire length of the same keratinous fibre, which may, in effect, be differently sensitized (i.e. damaged) between its end and its root.

Compositions for the oxidation dyeing of keratinous fibres at basic pH, containing an oxidation base such as para-phenylenediamine or para-aminophenol and 4-hydroxyindole as coupler, have already been proposed, in particular in German Patent Application DE 3,031,709. Such compositions are not, however, entirely satisfactory, in particular as regards the staying power of the colorations obtained with respect to the abovementioned external agents.

Compositions for the oxidation dyeing of keratinous fibres at acid pH, containing at least one oxidation dye precursor such as para-aminophenol or para-phenylene diamine and 4-hydroxyindole as coupler, have also been proposed already, in particular in French Patent FR 2,664, 304. Such compositions are not entirely satisfactory either, in particular as regards the selectivity of the colorations obtained.

The inventors have discovered discovered that it is possible to obtain new dyes which are especially resistant, in particular to perspiration, which create intense colorations showing little selectivity, by combining at least one oxidation dye precursor, chosen from 3-fluoro4-aminophenol and N,N'-bis(β-hydroxyethyl)-N,N'-bis(4'-aminophenyl)-1,3-diamino-2-propanol and their addition salts with an acid, with 4-hydroxyindole as coupler.

This discovery underlies the present invention.

Hence the subject of the invention is a composition for the oxidation dyeing of keratinous fibres, and especially human keratinous fibres such as hair, characterized in that it comprises, in a medium suitable for dyeing:
at least one oxidation dye precursor chosen from 3-fluoro4-aminophenol and N,N'-bis(β-hydroxyethyl)-N,N'-bis(4'-aminophenyl)-1,3-diamino-2-propanol and their addition salts with an acid;
4-hydroxyindole, as coupler.

The colorations obtained with the composition according to the invention display good dyeing power and excellent resistance properties both with respect to environmental agents such as light and inclement weather and with respect to perspiration and the different treatments which hair may undergo (washing, permanent-reshaping).

The subject of the invention is also a process for the oxidation dyeing of keratinous fibres employing this composition.

The addition salts with an acid which are usable in the context of the dyeing compositions of the invention are chosen, in particular, from the hydrochlorides, hydrobromides, sulphates and tartrates.

The collective oxidation dye precursors according to the invention, that is to say 3-fluoro-4-aminophenol and/or N,N'-bis(β-hydroxyethyl)-N,N'-bis(4'-aminophenyl)-1,3-diamino-2-propanol and/or its or their addition salts with an acid, preferably represent from 0.0005 to 10% by weight approximately of the total weight of the dyeing composition, and still more preferably from 0.01 to 5% by weight approximately.

The 4-hydroxyindole preferably represents from 0.0001 to 3.5% by weight approximately of the total weight of the dyeing composition, and still more preferably from 0.005 to 1% by weight approximately.

The medium suitable for dyeing (or vehicle) generally consists of water or of a mixture of water and least one organic solvent to solubilize compounds which might not be sufficiently soluble in water. As an organic solvent, there may be mentioned, for example, $C_1$–$C_4$ lower alkanols such as ethanol and isopropanol; glycerol; glycols and glycol ethers such as 2-butoxyethanol, propylene glycol, propylene glycol monomethyl ether and diethylene glycol monoethyl ether and monomethyl ether, as well as aromatic alcohols such as benzyl alcohol or phenoxyethanol, similar products and mixtures thereof.

Solvents may be present in proportions preferably of between 1 and 40% by weight approximately relative to the total weight of the dyeing composition, and still more preferably between 5 and 30% by weight approximately.

The pH of the dyeing composition as defined above is generally between 3 and 12. It may be adjusted to the desired value by means of acidifying or alkalinizing agents customarily used in the dyeing of keratinous fibres.

Among acidifying agents, there may be mentioned, by way of example, inorganic or organic acids such as hydrochloric acid, orthophosphoric acid, carboxylic acids such as tartaric acid, citric acid and lactic acid, and sulphonic acids.

Among alkalinizing agents, there may be mentioned, by way of example, aqueous ammonia, alkali metal carbonates, alkanolamines such as mono-, di- and triethanolamines as well as their derivatives, sodium or potassium hydroxide.

The dyeing composition according to the invention can also contain, in addition to the dyes defined above, other couplers and/or direct dyes, in particular to modify the shades or to enrich them with glints.

The dyeing composition according to the invention can also contain various adjuvants traditionally used in compositions for the dyeing of hair, such as anionic, cationic, nonionic, amphoteric or zwitterionic surfactants or mixtures thereof, anionic, cationic, nonionic, amphoteric or zwitterionic polymers or mixtures thereof, inorganic or organic thickening agents, antioxidants, penetrating agents, sequestering agents, perfumes, buffers, dispersing agents, conditioners, film-forming agents, preservatives and opacifying agents.

The dyeing composition according to the invention may be presented in various forms, for example in the form of liquids, creams or gels, or in any other form suitable for carrying out a dyeing of keratinous fibres, and human hair in particular.

The subject of the invention is also a process for the dyeing of keratinous fibres, and especially human keratinous fibres such as hair, employing the dyeing composition as defined above.

According to this process, the dyeing composition as defined above is applied to the fibres, the colour being developed at acid, neutral or alkaline pH using an oxidizing agent which is added to the dyeing composition just at the time of use or which is present in an oxidizing composition applied simultaneously or sequentially in a separate stage.

According to an especially preferred embodiment of the dyeing process according to the invention, the dyeing composition described above is mixed at the time of use with an oxidizing composition containing, in a medium suitable for dyeing, at least one oxidizing agent present in a sufficient amount to develop a coloration. The mixture obtained is then applied to the keratinous fibres and left in place for 3 to 40 minutes approximately, preferably 5 to 30 minutes approximately, after which the hair is rinsed, washed with shampoo, rinsed again and dried.

The oxidizing agent present in the oxidizing composition as defined above may be chosen from the oxidizing agents traditionally used for the oxidation dyeing of keratinous fibres, and among which hydrogen peroxide, urea peroxide, alkali metal bromates and persalts such as perborates and persulphates may be mentioned. Hydrogen peroxide is especially preferred.

The pH of the oxidizing composition containing the oxidizing agent as defined above is such that, after mixing with the dyeing composition, the pH of the resulting composition applied to the keratinous fibres preferably varies between 3 and 12 approximately, and still more preferably between 5 and 11. It is adjusted to the desired value by means of acidifying or alkalinizing agents customarily used in the dyeing of keratinous fibres, and such as are defined above.

The oxidizing composition as defined above can also contain various adjuvants traditionally used in compositions for the dyeing of hair, and such as are defined above.

The composition which is finally applied to the keratinous fibres may be presented in various forms, for example in the form of liquids, creams or gels, or in any other form suitable for carrying out a dyeing of keratinous fibres, and human hair in particular.

Another subject of the invention is a multi-compartment device or dyeing "kit" or any other multi-compartment packaging system in which a first compartment contains the dyeing composition as defined above and a second compartment contains the oxidizing composition as defined above. These devices may be equipped with a means enabling the desired mixture to be delivered onto the hair, such as the devices described in Patent FR-2,586,913 in the name of the Applicant.

The examples which follow are intended to illustrate the invention, no limitation of its scope being implied.

EXAMPLES

Examples 1 and 2

The following dyeing compositions 1 and 2 according to the invention were prepared (contents in grams):

| COMPOSITION | 1 | 2 |
|---|---|---|
| 3-Fluoro-4-aminophenol | 0.528 | |
| N,N'-Bis(β-hydroxyethyl)-N,N'-bis(4'-aminophenyl)-1,3-diamino-2-propanol tetrahydrochoride | | 0.4 |
| 4-Hydroxyindole | 0.520 | 0.4 |
| Common dyeing vehicle(*) | (*) | (*) |
| Water q.s. | 100 g | 100 g |

(*)common dyeing vehicle:

| | |
|---|---|
| Polyglycerolated oleyl alcohol containing 2 mol of glycerol | 4.0 g |
| Polyglycerolated oleyl alcohol containing 4 mol of glycerol, containing 78% of active substances(AS) | 5.69 g AS |
| Oleic acid | 3.0 g |
| Oleylamine containing 2 mol of ethylene oxide, sold under the trade name ETHOMEEN O12 by the company AKZO | 7.0 g |
| Diethylaminopropyl laurylamino-succinamate sodium salt containing 55% of AS | 3.0 g AS |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution containing 35% of AS | 0.455 g AS |
| Ammonium acetate | 0.8 g |
| Antioxidant, sequestering agent | q.s. |
| Perfume, preservative | q.s. |
| Aqueous ammonia containing 20% of $NH_3$ | 10.0 g |

At the time of use, each dyeing composition was mixed with an equal amount of an oxidizing composition consisting of 20-volumes (6% by weight) hydrogen peroxide solution.

Each resulting mixture was applied for 30 minutes to locks of natural or permanent-waved grey hair which was 90% white. Thereafter the locks of hair were rinsed, washed with a standard shampoo and then dried.

The locks of hair were dyed in the shades appearing in the table below:

| EXAMPLE (COMPOSITION) | SHADE ON NATURAL HAIR | SHADE ON PERMANENT-WAVED HAIR |
|---|---|---|
| 1 (1) | light coppery iridescent | coppery iridescent |
| 2 (2) | light bluish ashen | ashen blue |

Example 3

The following dyeing composition according to the invention was prepared:

| | |
|---|---|
| N,N'-Bis(β-hydroxyethyl)-N,N'-bis(4'-aminophenyl)-1,3-diamino-2-propanol tetrahydrochloride | 1 g |
| 4-Hydroxyindole | 0.26 g |
| Polyglycerolated oleyl alcohol containing 2 mol of glycerol | 4.0 g |

-continued

| | |
|---|---|
| Polyglycerolated oleyl alcohol containing 4 mol of glycerol, containing 78% of active substances (AS) | 5.69 g AS |
| Oleic acid | 3.0 g |
| Oleylamine containing 2 mol of ethylene oxide, sold under the trade name ETHOMEEN O12 by the company AKZO | 7.0 g |
| Diethylaminopropyl laurylamino-succinamate sodium salt containing 55% of AS | 3.0 g AS |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqeuous solution containing 35% of AS | 0.455 g AS |
| Ammonium acetate | 0.8 g |
| Antioxidant, sequestering agent | q.s. |
| Perfume, preservative | q.s. |
| Monoethanolamine q.s. | pH 9.8 |
| Demineralized water q.s. | 100 g |

At the time of use, this dyeing composition was mixed with an equal amount of an oxidizing composition consisting of 20-volumes (6% by weight) hydrogen peroxide solution, the pH of which was adjusted to between 1 and 1.5 with 2.5 g of orthophosphoric acid per 100 g of hydrogen peroxide.

The resulting mixture had a pH of 6.2, and was applied for 30 minutes to locks of natural grey hair which was 90% white. Thereafter the locks of hair were rinsed, washed with a standard shampoo and then dried.

The locks of hair were dyed in an ashen blue shade.

Comparative Examples 4 and 5

The following dyeing compositions 4 and 5 were prepared:

| | |
|---|---|
| Dyeing composition 4 according to the invention: | |
| 3-Fluoro-4-aminophenol | 0.508 g |
| 4-Hydroxyindole | 0.520 g |
| Common dyeing vehicle defined in Examples 1 and 2 above | (*) g |
| Demineralized water q.s. | 100 g |
| Dyeing composition 5 not forming part of the invention: | |
| para-Aminophenol | 0.5 g |
| 4-Hydroxyindole | 0.520 g |
| Common dyeing vehicle defined in Examples 1 and 2 above | (*) g |
| Demineralized water q.s. | 100 g |

At the time of use, each dyeing composition was mixed with an equal amount of an oxidizing composition consisting of 20-volumes (6% by weight) hydrogen peroxide solution.

Each resulting mixture was applied for 30 minutes to locks of natural grey hair which was 90% white. Thereafter the locks of hair were rinsed, washed with a standard shampoo and then dried.

The colour of the locks was then evaluated in the MUNSELL system by means of a MINOLTA CM 2002 colorimeter.

The locks of hair thus dyed were then subjected to a perspiration resistance test.

To this end, the locks of hair were immersed in a crystallizing dish covered with a watch glass and containing a synthetic sweat solution of the following composition:

| | |
|---|---|
| NaCl | 10 g |
| Potassium hydrogen phosphate | 1 g |
| Histidine | 0.25 g |
| Lactic acid q.s. | pH 3.2 |
| Distilled water q.s. | 100 g |

The locks of dyed hair were left standing in this synthetic sweat solution for 48 hours at 37° C. Thereafter the locks were rinsed and then dried.

The colour of the locks was then evaluated again in the MUNSELL system by means of a MINOLTA CM 2002 calorimeter so as to determine the degradation of the colorations after this perspiration resistance test.

According to the MUNSELL notation, a colour is defined by the expression HV/C, in which the three parameters denote, respectively, the tint or hue (H), the intensity or value (V) and the purity or chroma (C); the oblique stroke in this expression is simply a convention and does not indicate a ratio.

The difference in colour between two locks is calculated by applying the NICKERSON formula: $\Delta E=0.4\ Co\Delta H + 6\Delta V + 3\ \Delta C$, as described, for example, in "Couleur, Industrie et Technique" [Colour, Industry and Technique], pages 14–17, vol. No. 5, 1978.

In this formula, $\Delta E$ represents the difference in colour between two locks, $\Delta H$, $\Delta V$ and $\Delta C$ represent the variation in absolute value of the parameters H, V and C, and Co represents the purity of the lock relative to which it is desired to evaluate the difference in colour.

The results are given in the table below:

| EXAMPLE (COMPO-SITION) | Hair colour before the test | Hair colour after the test | Degradation of the colour | | | |
|---|---|---|---|---|---|---|
| | | | $\Delta H$ | $\Delta V$ | $\Delta C$ | $\Delta E$ |
| 4 (4) | 0.1 YR 4.4/3.3 | 1.2 YR 4.1/3.0 | 1.1 | 0.3 | 0.3 | 4.15 |
| 5 (5) | 9.7 R 4.2/3.2 | 0.4 YR 3.3/2.3 | 0.7 | 0.9 | 0.9 | 9 |

These results show that the composition of Example 4 according to the invention leads to a coloration which withstands perspiration much better than the composition of Example 5, which does not form part of the invention and is as described, for example, in German Patent Application DE 3,031,709.

What is claimed is:

1. A composition for the oxidation dyeing of keratinous fibres, comprising, in a medium suitable for dyeing,
   at least one oxidation dye precursor of 3-fluoro-4-aminophenol and N,N'-bis(β-hydroxyethyl)-N,N'-bis(4'-aminophenyl)-1,3-diamino-2-propanol or their addition salts with an acid, and
   4-hydroxyindole, as a coupler.

2. A composition according to claim 1, wherein the keratinous fibres are human hair.

3. A composition according to claim 1, wherein the addition salts with an acid are hydrochlorides, hydrobromides, sulphates or tartrates.

4. A composition according to claim 1, wherein the amount of the oxidation dye precursor ranges from about 0.0005 to 10% by weight of the total weight of the composition.

5. A composition according to claim 4, wherein the amount of the oxidation dye precursor ranges from about 0.01 to 5% by weight of the total weight of the composition.

6. A composition according to claim 1, wherein the amount of the 4-hydroxyindole ranges from about 0.0001 to 3.5% by weight of the total weight of the composition.

7. A composition according to claim 6, wherein the amount of the 4-hydroxyindole ranges from about 0.005 to 1% by weight of the total weight of the dyeing composition.

8. A composition according to claim 1, wherein the medium suitable for dyeing comprises water or a mixture of water and at least one organic solvent selected from $C_1$–$C_4$ lower alkanols, glycerol, glycols and glycol ethers, aromatic alcohols, and mixtures thereof.

9. A composition according to claim 1, wherein the composition has a pH ranging from about 3 to 12.

10. A composition according to claim 9, wherein the pH ranges from about 5 to 11.

11. A process for the dyeing of keratinous fibres, comprising the step of applying to the fibres a composition as claimed in claim 1, wherein colour from the dyeing composition develops at acid, neutral or alkaline pH.

12. A process according to claim 11, wherein the oxidizing agent is added to the composition at the time of use of the composition.

13. A process according to claim 11, wherein the oxidizing agent is added simultaneously with the dyeing composition or sequentially in a separate step.

14. A process according to claim 12, wherein the oxidizing agent is hydrogen peroxide, urea peroxide, alkali metal bromate or a persalt.

15. A process according to claim 14, wherein the persalt is perborate or persulphate.

16. A process according to claim 13, wherein the oxidizing agent is hydrogen peroxide, urea peroxide, alkali metal bromate or a persalt.

17. A process according to claim 16, wherein the persalt is perborate or persulphate.

18. A multi-compartment dyeing kit, comprising a first compartment containing a dyeing composition as claimed claim 1, and a second compartment containing an oxidizing composition.

* * * * *